United States Patent

Mejslov

[11] Patent Number: 6,123,690
[45] Date of Patent: *Sep. 26, 2000

[54] SUBCUTANEOUS INFUSION DEVICE

[75] Inventor: Jesper Mejslov, Roskilde, Denmark

[73] Assignee: Maersk Medical A/S, Lynge, Denmark

[*] Notice: This patent issued on a continued prosecution application filed under 37 CFR 1.53(d), and is subject to the twenty year patent term provisions of 35 U.S.C. 154(a)(2).

[21] Appl. No.: 09/045,756

[22] Filed: Mar. 20, 1998

[51] Int. Cl.⁷ .................................................. A61M 25/00
[52] U.S. Cl. ................... 604/283; 128/DIG. 26; 604/114
[58] Field of Search ..................... 604/167, 174, 604/178, 179, 180, 283, 905, 414, 256; 128/DIG. 26

[56] References Cited

U.S. PATENT DOCUMENTS

| | | | |
|---|---|---|---|
| 3,927,660 | 12/1975 | Tegtmeyer | 128/DIG. 26 |
| 4,397,641 | 8/1983 | Jacobs | 604/180 |
| 4,673,400 | 6/1987 | Martin | 604/905 |
| 5,449,349 | 9/1995 | Sallee et al. | 604/180 |
| 5,522,803 | 6/1996 | Teissen-Simony | 604/177 |
| 5,545,143 | 8/1996 | Fischell | 604/180 |
| 5,776,116 | 7/1998 | Lopez et al. | 604/411 |

FOREIGN PATENT DOCUMENTS

| | | | |
|---|---|---|---|
| 0023580 | 2/1981 | European Pat. Off. | 604/177 |
| WO 91/16939 | 11/1991 | WIPO | 604/180 |

*Primary Examiner*—Wynn Wood Coggins
*Assistant Examiner*—Sharon Finkel
*Attorney, Agent, or Firm*—Brinks, Hofer, Gilson & Lione

[57] ABSTRACT

The invention relates to a subcutaneous infusion device comprising: a housing, a flow channel within the housing, a cannula extending from the housing and being in flow communication with the flow channel, a self-sealing septum covering the flow channel, a connector for delivery of fluid into the flow channel, a needle on the connector for penetrating the self-sealing septum covering the flow channel in the housing, a guide means for guiding the connector with the needle into a correct position in relation to the housing, where the guide means has incorporated means for interlocking the connector and the housing. Hereby a simpler and easier operable product is obtained.

2 Claims, 18 Drawing Sheets

SUBCUTANEOUS INFUSION DEVICE

BACKGROUND OF THE INVENTION

The present invention relates to infusion devices for subcutaneous delivery of a medication or a therapeutic fluid by means of an external infusion system and more particularly to an infusion device having releasably connected means for delivery of the medication or the therapeutic fluid from the external infusion system.

Infusion devices are generally known in the art for delivering a medication or a therapeutic fluid to a subcutaneous site in a patient by means of a cannula inserted through the patients skin to the subcutaneous site. Such devices commonly comprise a tubular cannula extending from a housing adapted to receive the desired medication via disconnectable means for suitable connection to further components of the infusion system. The possibility of disconnecting the infusion device from the further parts of the infusion system is provided in order to improve the user comfort. The user is enabled to perform activities which do not allow the presence of a pump or the like, or which are hindered by the presence of a pump or the like. In the disconnected state only a part of the infusion device is worn by the patient. This allows for increased mobility. In order to provide such disconnectable means and still maintain a fluid-tight sealing towards the interior of the housing and the tubular cannula that prevents contamination of the infusion site, such devices are commonly provided with a self-sealing penetrable septum on either the housing or the disconnectable part and a hollow needle on the other part adapted to penetrate the septum. Upon withdrawal of the needle from the septum this provides a fluid-tight sealing towards the interior of the housing. The septum and the needle further provides a fluid-tight sealing between the housing and the connector means when medication or therapeutic fluid is delivered to the patient from the external infusion system. Upon connection of the connector in relation to the housing the needle is inserted through the septum. In order to facilitate the placement and to ensure the correct penetration site for the a needle guide means is provided on either the housing or the connector. Further locking means are provided in order to secure the position of the connector in relation to the housing. Subcutaneous infusion devices of this generally known type are disclosed in e.g. U.S. Pat. No. 5,522,803 to Teissen-Simony and U.S. Pat. No. 5,545,143 to Fischell.

The manufacture of such a device is connected with problems since small dimensions are required in order to satisfy the user need for an mainly not visible device. Although the presently known infusion devices to some extent provide a help during the connection of the connector in relation to the housing, the assembling of the housing and the connector is due to these small dimensions still connected with great difficulty especially for patients with reduced sight or physical handicaps.

For these reasons there is a need for improvements in the infusion devices of the type mentioned in the foregoing, and particularly with respect to providing an infusion device which is far less cumbersome from a manufacturing point of view and which provides for a simplified connecting process while maintaining the desired small dimensions of such an infusion device. The infusion device according to the invention remedies the above mentioned disadvantages and provides further advantages which will become apparent from the following description.

SUMMARY OF THE INVENTION

According to the invention a subcutaneous infusion device has been developed wherein said subcutaneous infusion device comprises:
a housing;
a flow channel within the housing;
a cannula extending from the housing and being in flow communication with the flow channel;
a connector for delivery of fluid into the flow channel;
a guide means for guiding the connector with the needle into a correct position in relation to the housing;
where the guide means has incorporated means for interlocking the connector and the housing.

By incorporating the locking means in the guide means a much simpler construction can be obtained. At the same time the handling of the device has been simplified since there is no longer a need for observing several independent functional elements during the connection of the connector to the housing and since the combined guide and locking element can be configured somewhat larger within the limited dimensions of such a device.

In a preferred embodiment the infusion device comprises a self-sealing septum covering the flow channel and a needle on the connector for penetrating the self-sealing septum covering the flow channel in the housing. This embodiment ensures a proper sealing and a proper delivery through the sealing.

In one preferred embodiment the guide means comprises at least one elongate flexible element having a barb, and wherein the housing comprises a recess for receiving the elongate flexible element and an aperture for interacting with the barb on the elongate flexible element. In another preferred embodiment the guide means comprises two elongate flexible elements each having a barb, and wherein the housing comprises two recesses for receiving the elongate flexible elements and locking edges for interacting with the barb on each elongate flexible element.

In both embodiments it is a possibility that each of the elongate flexible elements comprises a bending area and a pivoting area mutually adapted to bring the barbs out of engagement upon effecting a pressure on the bending area hereby pivoting the outer end of each arm.

In a preferred embodiment each elongate flexible element is placed so as to cover the needle. Hereby harmful injuries caused by the needle are avoided to the widest possible extent.

In order to provide a guiding effect the housing can comprise grooves parallel with the bore and on the connector fins adapted for corresponding with the grooves. Another possibility comprises grooves in the connector parallel with the bore and on the housing fins adapted for corresponding with the grooves.

The infusion device is preferably connected to the patient by means of an adhesive material.

The infusion device according to the invention will in the following be explained more detailed with reference to the drawings showing a preferred embodiment.

DESCRIPTION OF THE PREFERRED EMBODIMENTS

Figure 1:
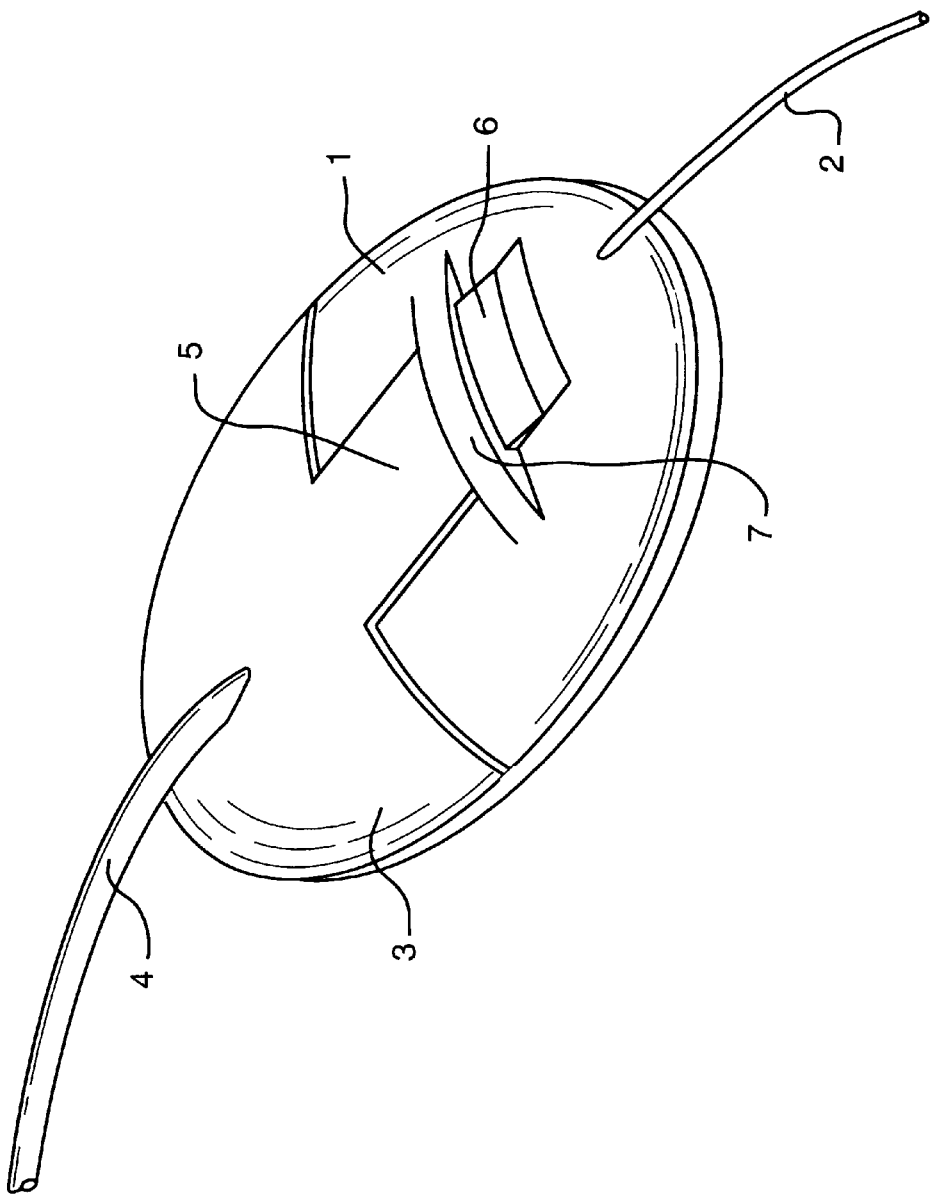
FIG. 1 is a perspective view of a preferred embodiment of the subcutaneous infusion device according to the invention.

It appears from FIG. 1 that the first embodiment of the infusion device comprises a housing 1 and a soft cannula 2 extending from the housing. A connector 3 is connected to the housing and a hose 4 extends from the connector for providing fluid communication between a pump (not shown) and the connector.

Figure 2:
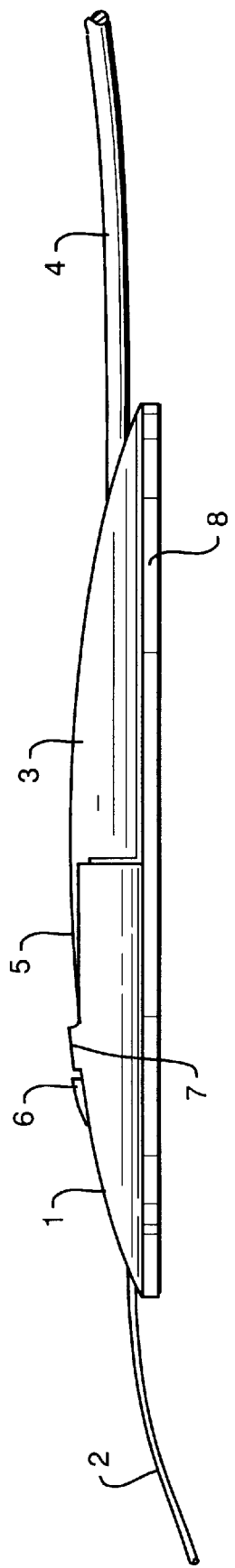
FIG. 2 is a side view of the device shown in FIG. 1.

From FIG. 2 it appears that locking arm 5 on the connector comprises a barb 6 co-operating with a transverse bridge element 7 delimiting a recess in the housing. In order to release the connector the locking arm 5 must be pressed down while the connector 3 is retracted from the housing.

Figure 3:
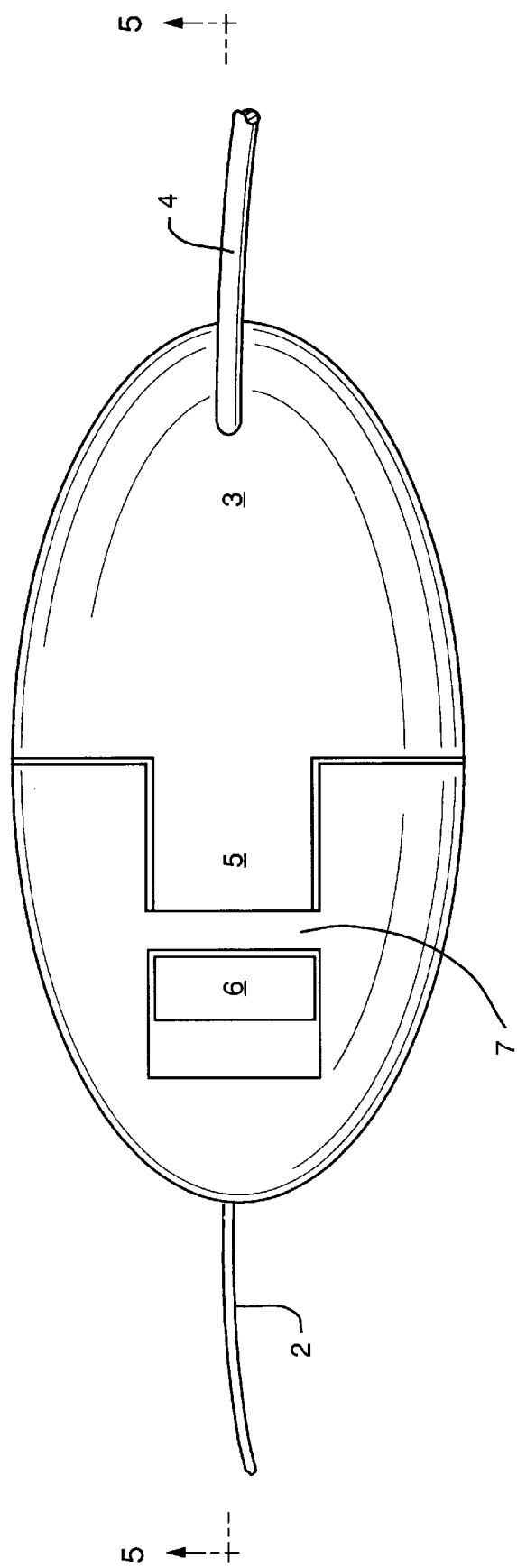
FIG. 3 is a top view of the device shown in FIG. 1.

From FIG. 3 it appears that the device has a substantially elliptic ground shape. The device could however have any ground shape allowing the providing of a bore, a self-sealing septum and the cannula in the housing and a bore, a hose and a needle in the connector and furthermore the combined guide and locking means in connection with the housing and the connector.

Figure 4:
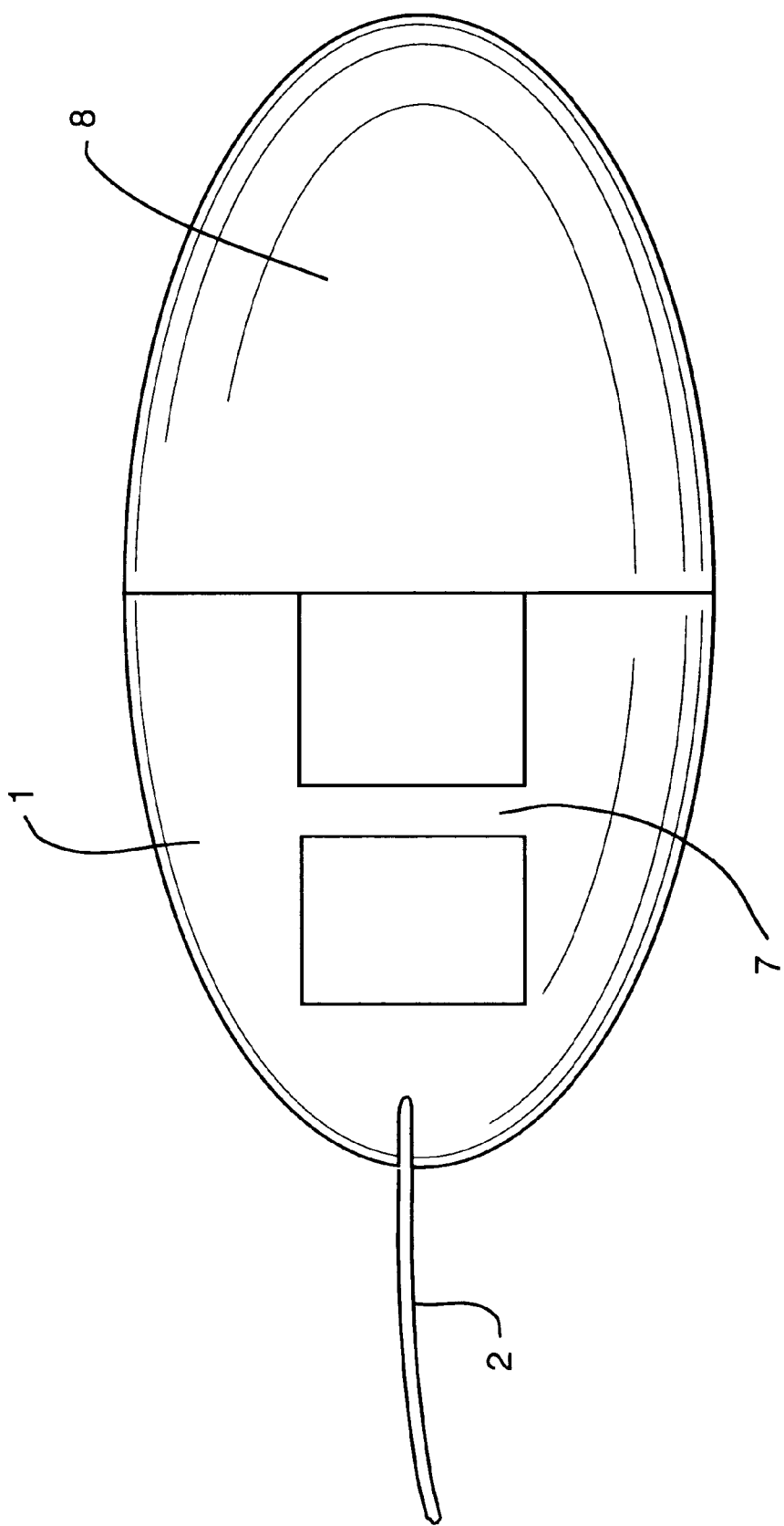
FIG. 4 is a top view of the housing of the device shown in FIG. 1.

From FIG. 4 the housing appears after the connector has been released from the device. It appears that the housing comprises a backwards extending platform 8 intended for the support of the connector in the mounted state of this.

Figure 5:
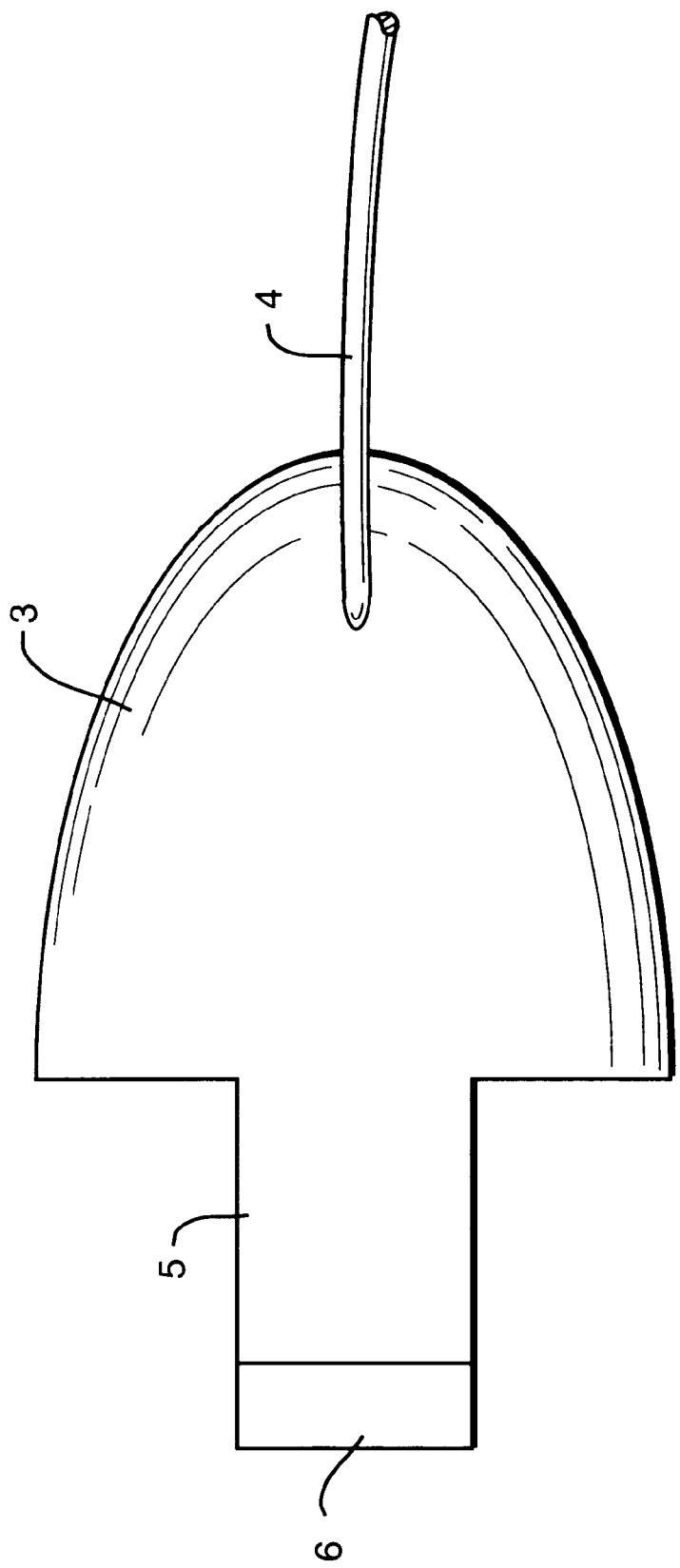
FIG. 5 is a top view of the connector of the device shown in FIG. 1.

From FIG. 5 the connector appears after the release from the housing. The flexible locking arm 5 extends beyond a needle 14 (see FIG. 6), hereby providing a protective shield against harmful injuries caused by the needle 14.

Figure 6:
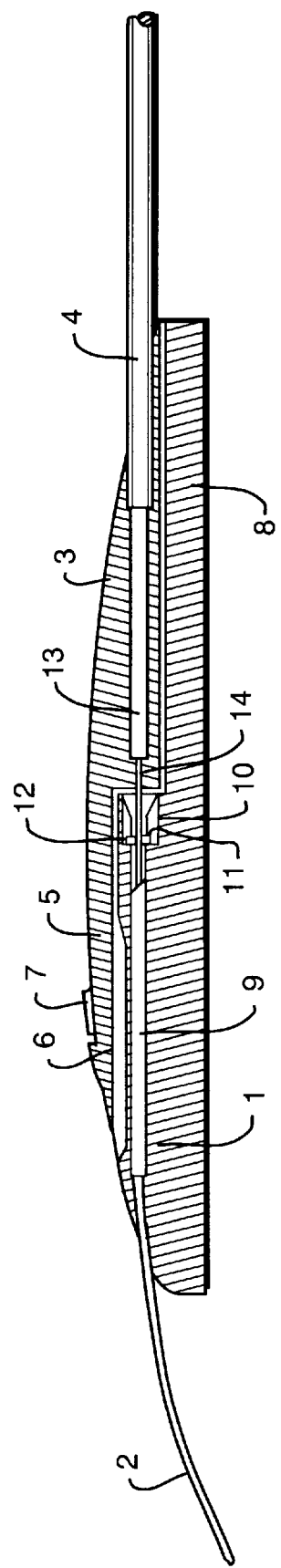
FIG. 6 is a sectional view along the line 5—5 in FIG. 3.

From FIG. 6 it appears that the housing 1 is provided with a bore, where at one end of this bore the soft cannula 2 is mounted in flow communication with the bore 9. At the end of the bore opposite the soft cannula 2 a self-sealing septum 11 is mounted. The connector 3 comprises a bore 13 where the hose 4 is connected in fluid communication with this bore 13 at one end of this and where at the other end of the bore opposite the hose 4 a hollow needle 14 is provided in fluid communication with the bore 13. The needle 14 is provided for penetrating the self-sealing septum 11 in the housing 1. The self-sealing septum 11 provides a fluid and air seal towards the surroundings when the needle of the connector 3 is retracted from the septum 11 and further provides a air and fluid seal around the needle when inserted through the septum.

Figure 7:
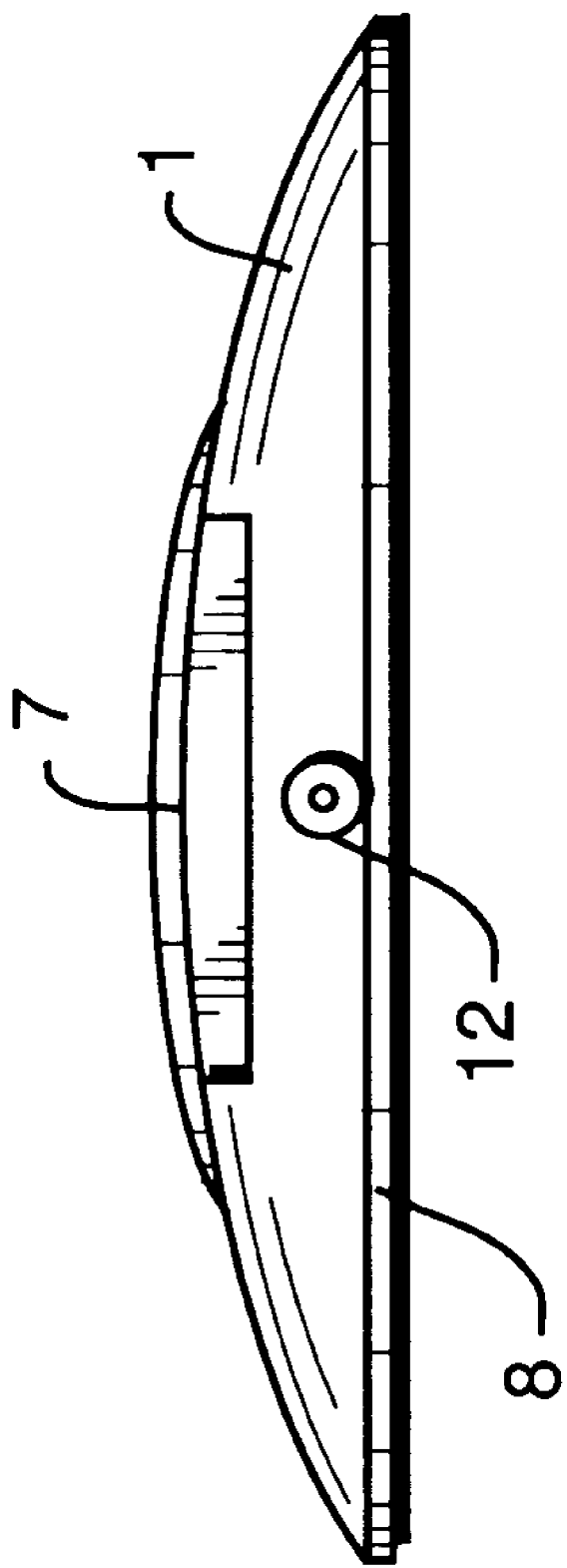
FIG. 7 is a rear end view of the housing of the device shown in FIG. 1.

From FIG. 7 the rear end of the housing appears. A conical entrance 10 for the needle 14 is visualised as well as the recess for the flexible guide and locking arm 5.

Figure 8:
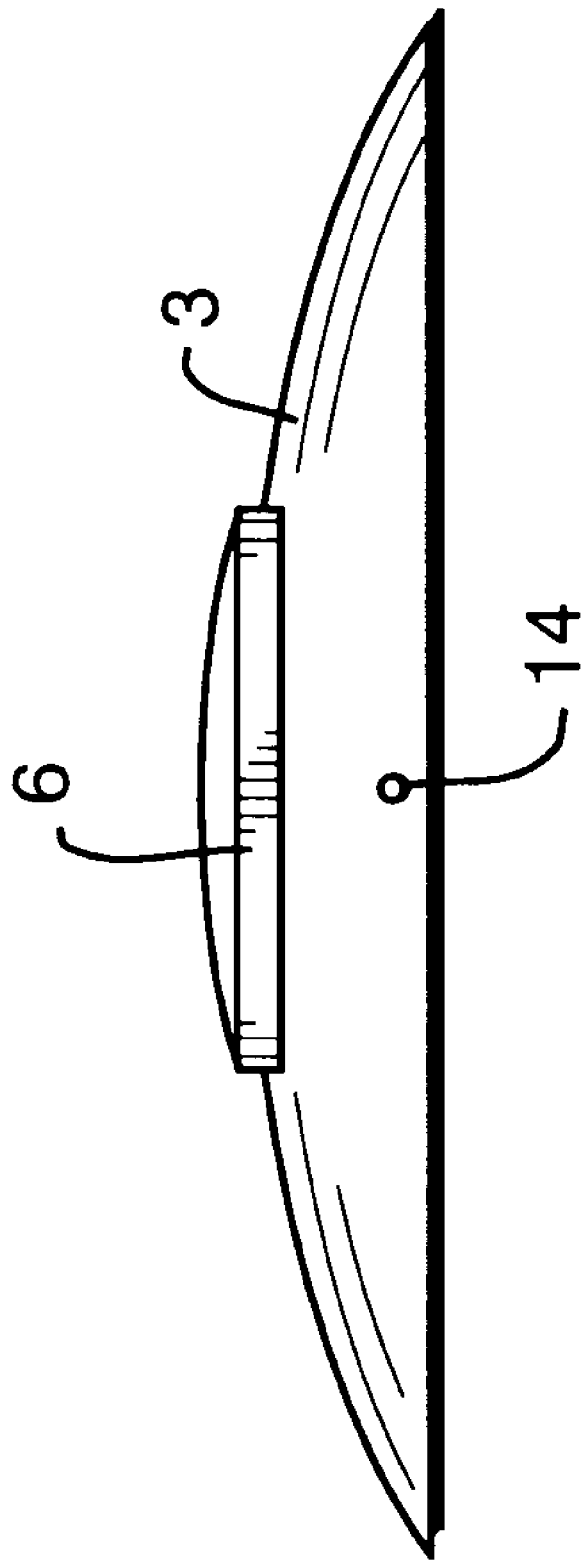
FIG. 8 is a front end view of the connector of the device shown in FIG. 1.

From FIG. 8 the front end of the connector 3 appears. The needle 14 and the flexible guide and locking arm are visualised.

Figure 9:
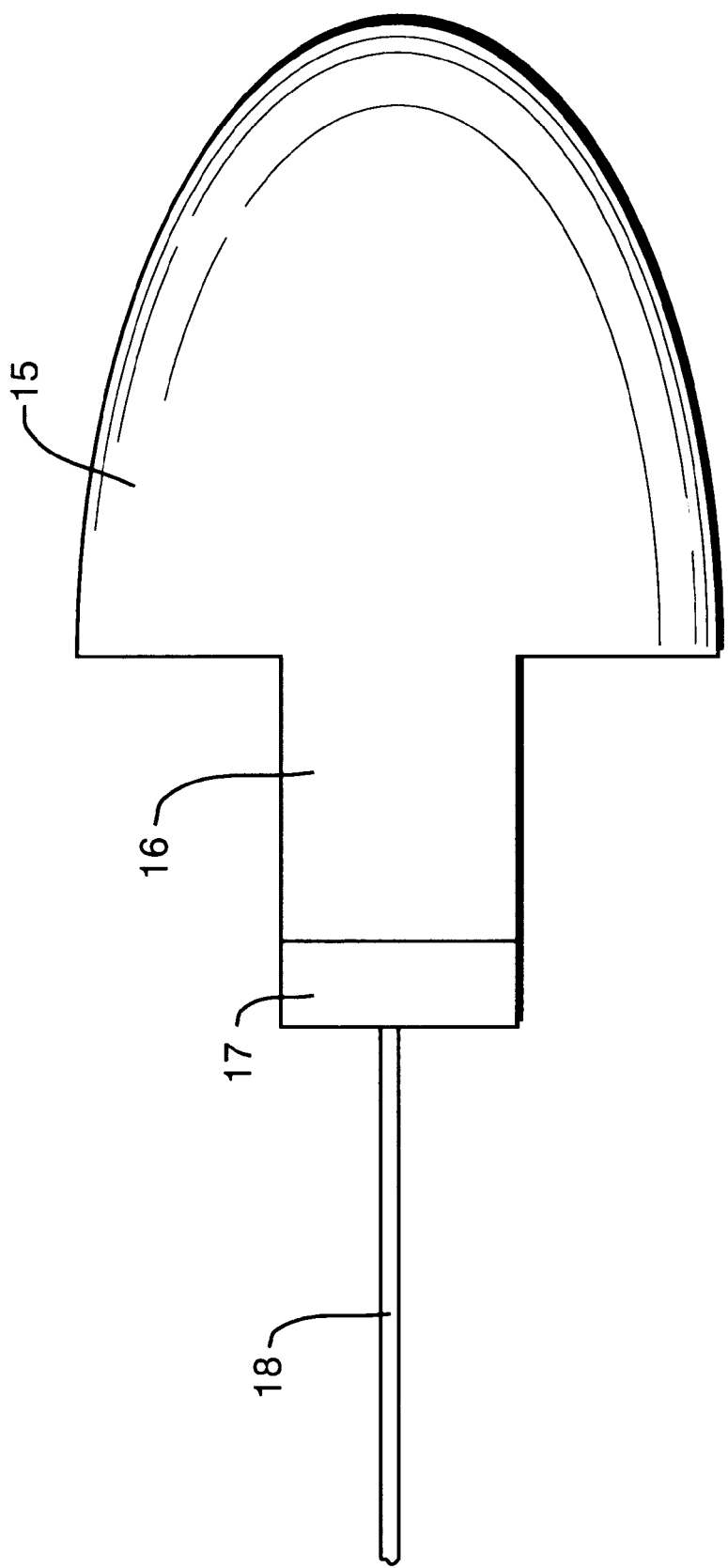
FIG. 9 is a top view of an insertion needle for use in connection with the device shown in FIG. 1.

From FIG. 9 an insertion needle 18 for use in connection with the device shown in FIG. 1 appears. The insertion needle comprises a needle hub 15 adapted to interact with housing 1 in the same manner as the connector, i.e. by means of a single elongate flexible element 3. The needle 18 extends through the soft cannula beyond the outer tip of this in the insertion position.

Figure 10:
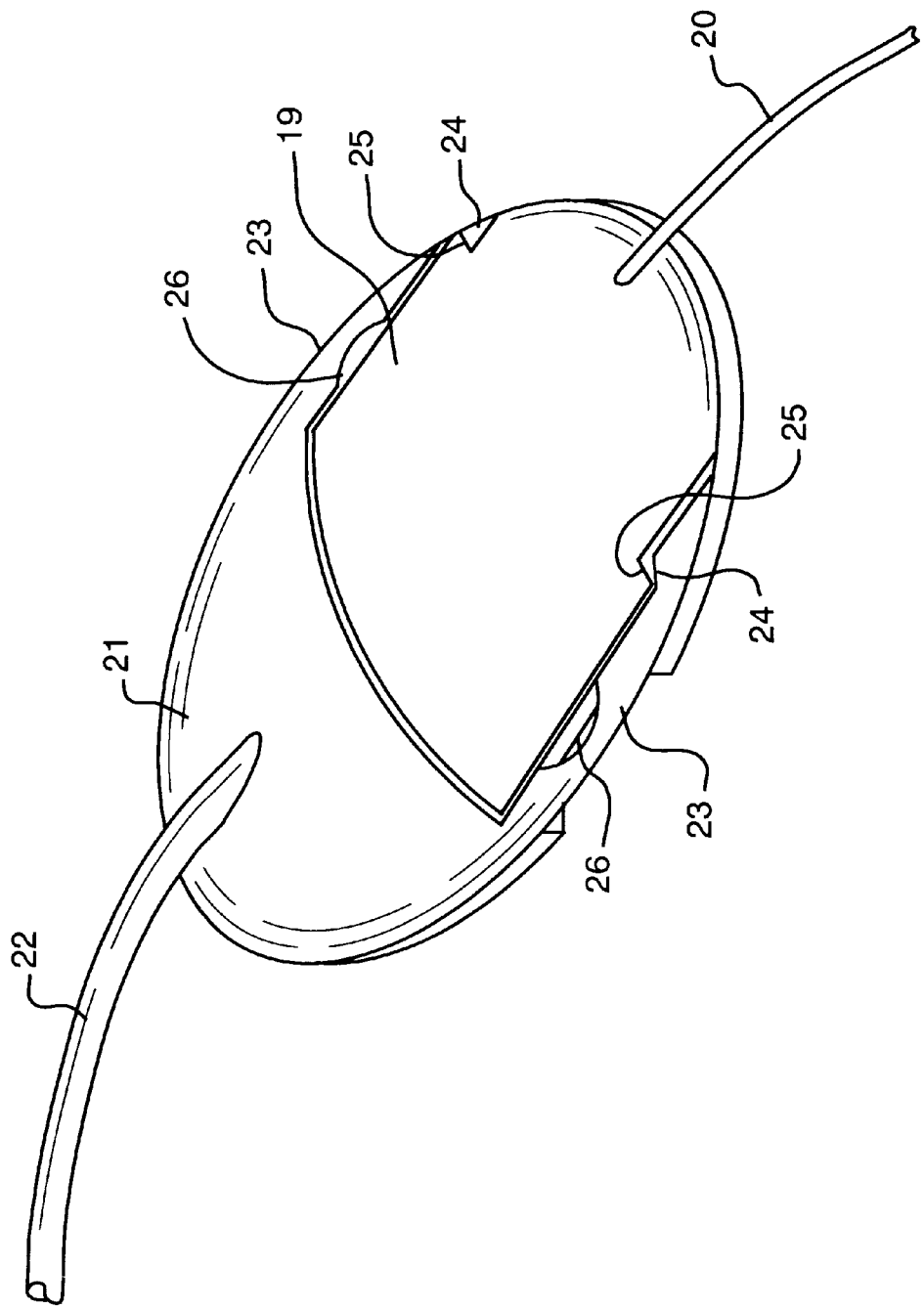
FIG. 10 is a perspective view of a preferred embodiment of the subcutaneous infusion device according to the invention.

It appears from FIG. 10 that the second embodiment of the infusion device comprises a housing 19 and a soft cannula 20 extending from the housing. A connector 3 is connected to the housing and a hose 22 extends from the connector for providing fluid communication between a pump (not shown) and the connector.

Figure 11:
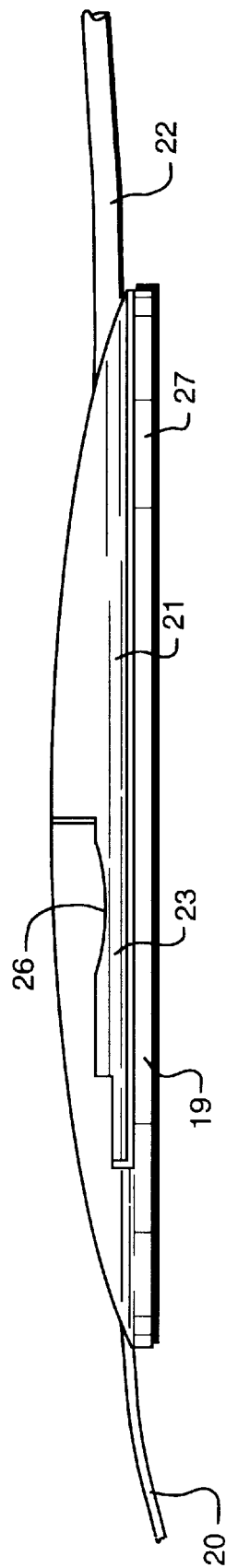
FIG. 11 is a side view of the device shown in FIG. 10.

From FIG. 11 it appears two locking arms 23 on the connector each having an barb 24 co-operating with a edge 25 in the housing, form combined guide and locking means. In order to release the connector the locking arms must be pressed towards each other while the connector is retracted from the housing.

Figure 12:
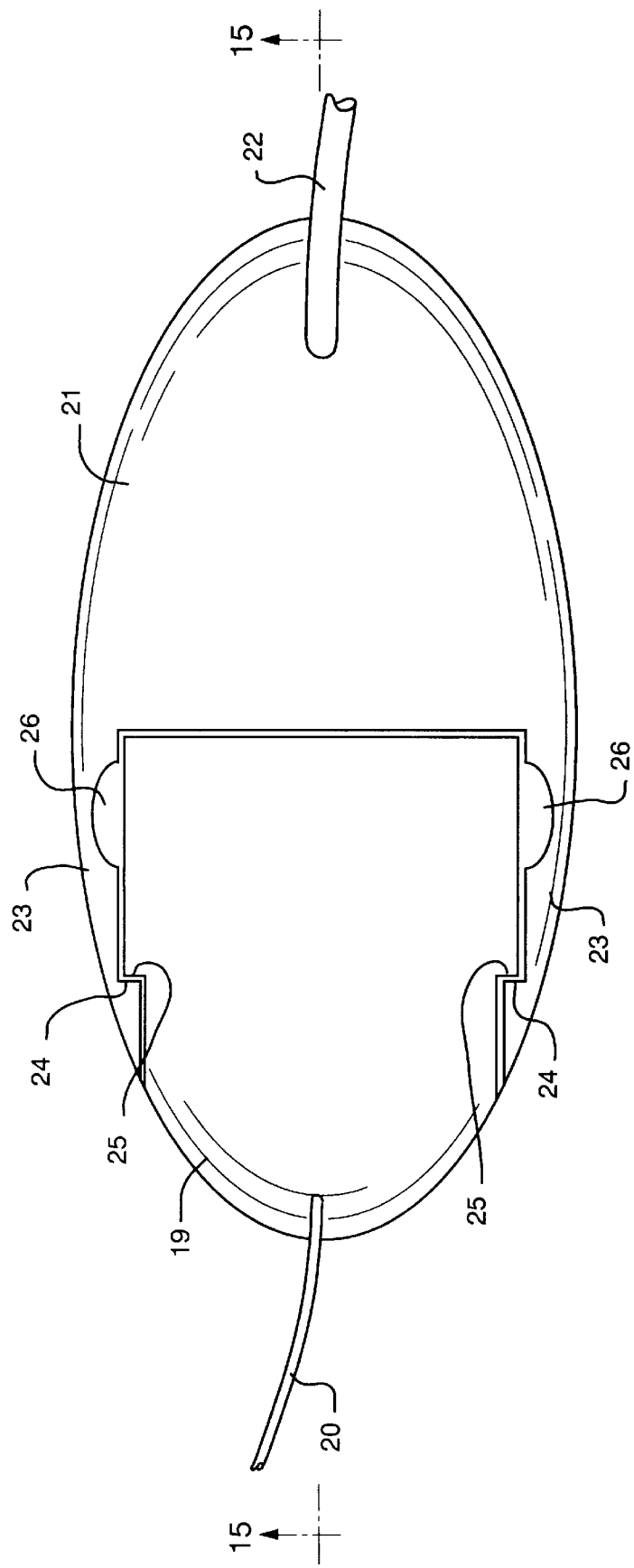
FIG. 12 is a top view of the device shown in FIG. 10.

From FIG. 12 it appears that the device has a substantially elliptic ground shape. The device could however have any ground shape allowing the providing of a bore 31, a self-sealing septum 32 and the cannula 20 in the housing and the bore 25, the hose 22 and the needle 30 in the connector and furthermore the combined guide and locking means in connection with the housing and the connector.

Figure 13:
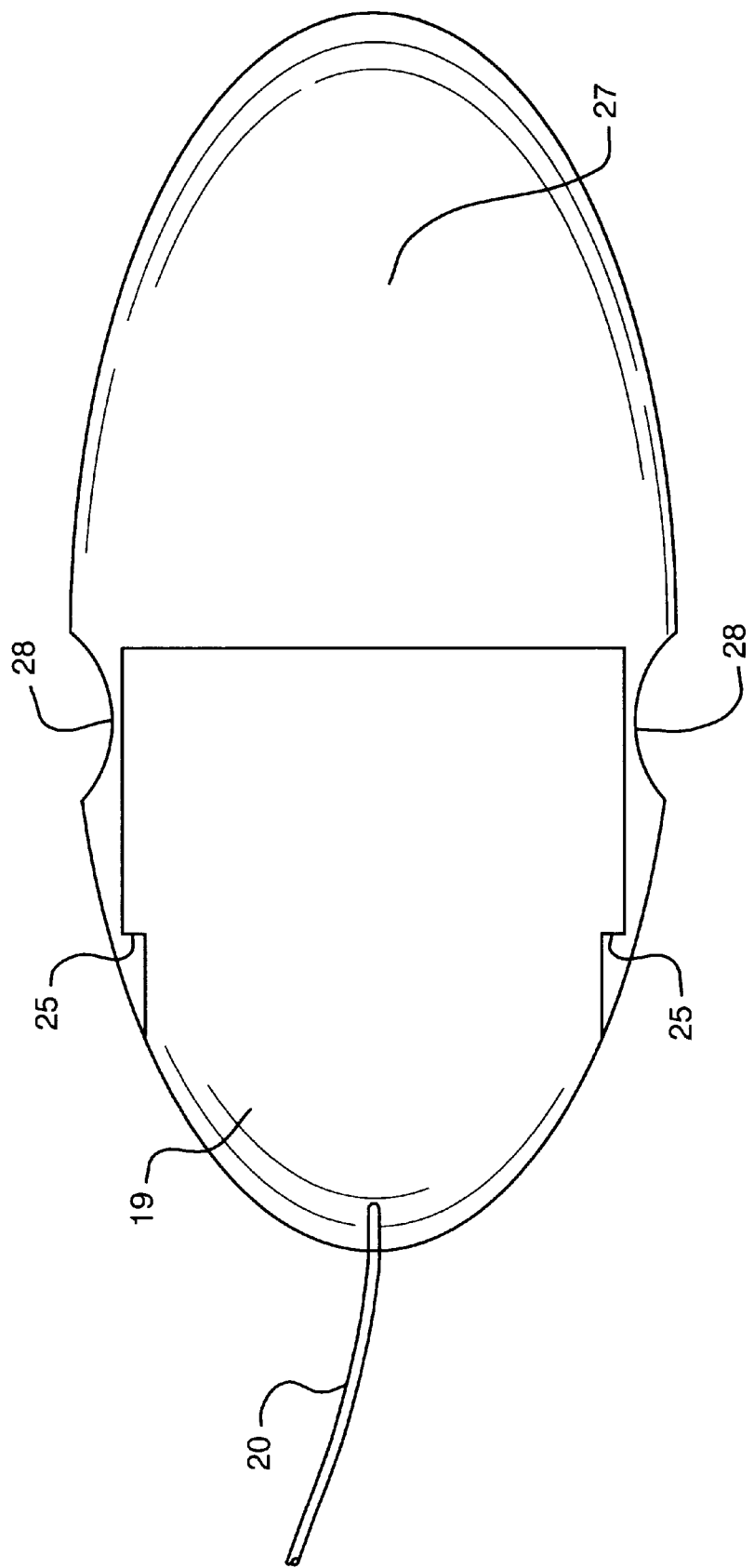
FIG. 13 is a top view of the housing of the device shown in FIG. 10.

From FIG. 13 the housing appears after the connector has been released from the device. It appears that the housing comprises a backwards extending platform 27 intended for the support of the connector in the mounted state of this.

Figure 14:
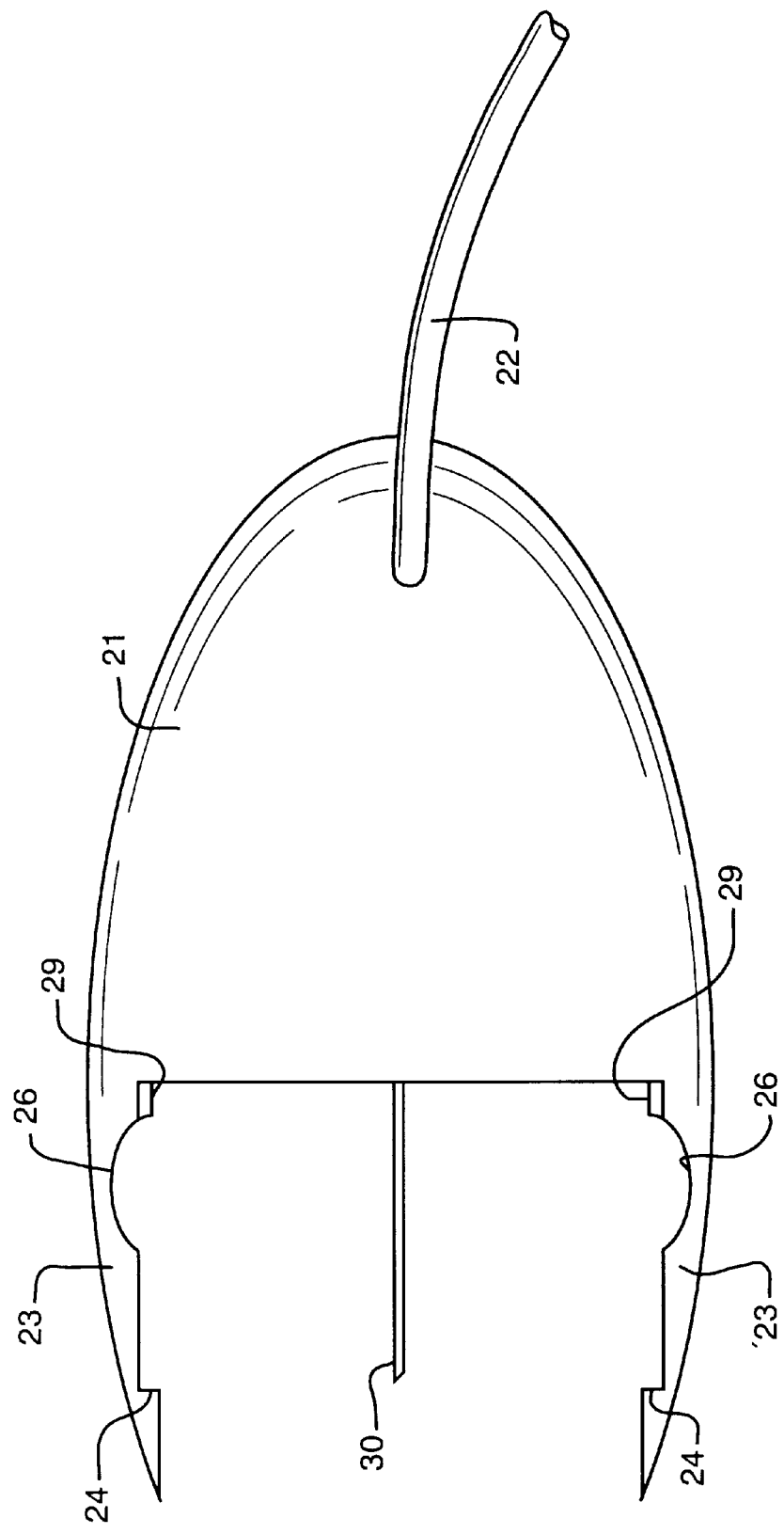
FIG. 14 is a top view of the connector of the device shown in FIG. 10.

From FIG. 14 the connector appears after the release from the housing. It appears that the flexible locking arms 23 extends beyond the needle, hereby providing a protective shield against harmful injuries caused by the needle 30.

Figure 15:
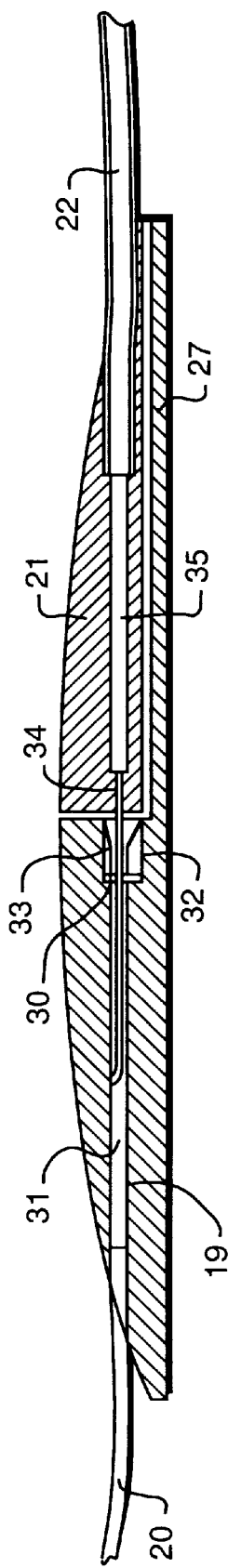
FIG. 15 is a sectional view along the line 16—16 in FIG. 13.

From FIG. 15 it appears that the housing is provided with a bore 35, where at one end of this bore the soft cannula 2 is mounted in flow communication with the bore. At the end of the bore opposite the soft cannula 2 a self-sealing septum is mounted. The connector comprises a bore where the hose 4 is connected in fluid communication with this bore at one end of this and where at the end of the bore opposite the hose a hollow needle is provided in fluid communication with the bore. The needle is provided for penetrating the self-sealing septum 32 in the housing. The self-sealing septum provides a fluid and air seal towards the surroundings when the needle of the connector is retracted from the septum and further provides a air and fluid seal around the needle when inserted through the septum.

Figure 16:
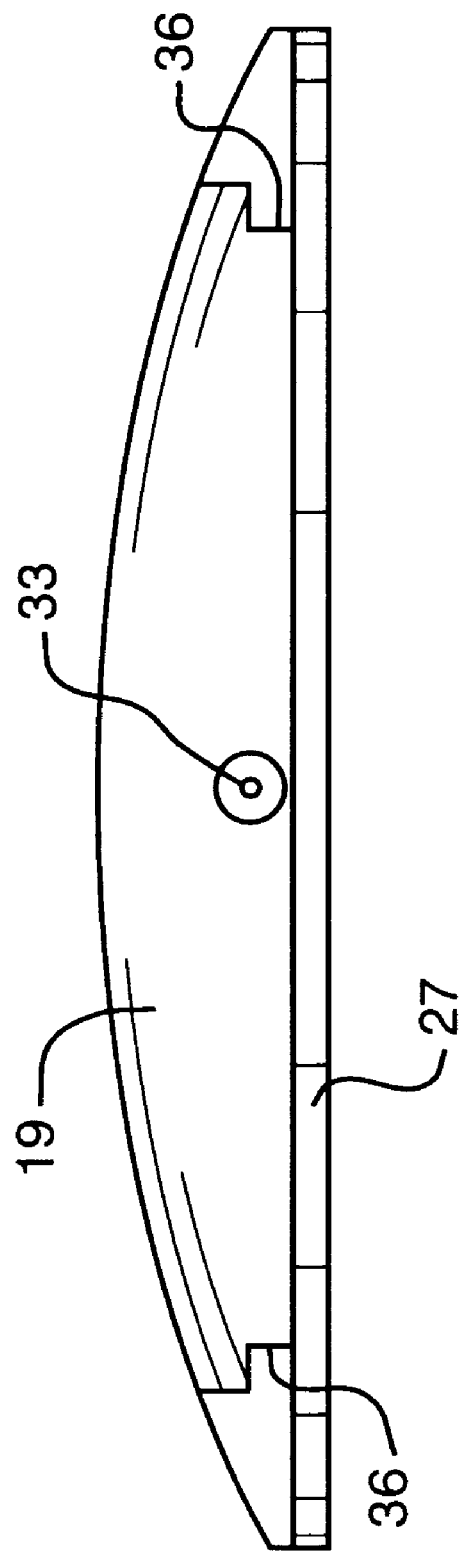
FIG. 16 is a rear end view of the housing of the device shown in FIG. 9.

From FIG. 16 the rear end of the housing appears. The conical entrance for the needle is visualised as well as grooves 36 for the flexible guide and locking arms.

Figure 17:
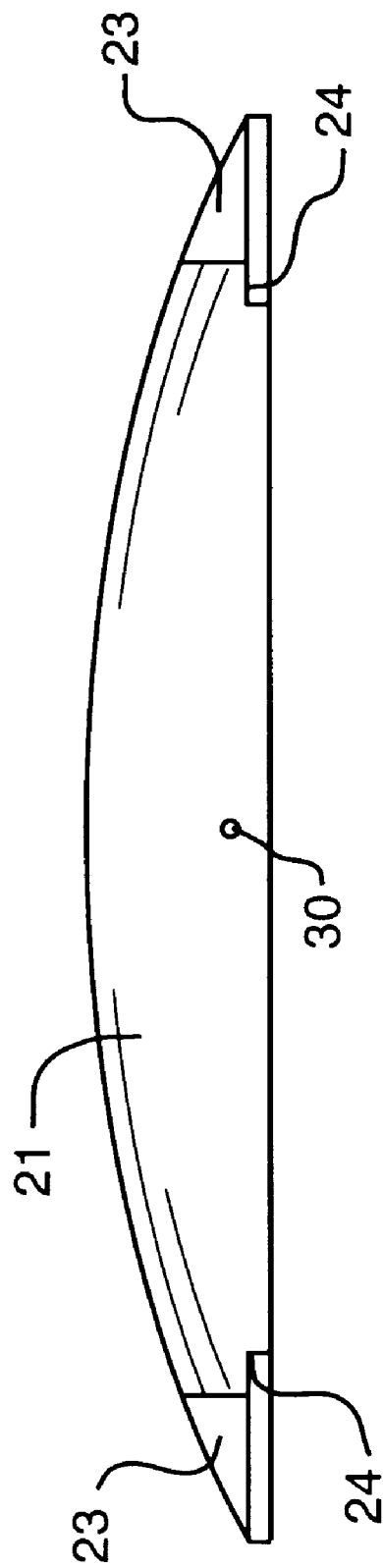
FIG. 17 is a front end view of the connector of the device shown in FIG. 9.

From FIG. 17 the front end of the connector appears. The needle 30 and the flexible guide and locking arms 23 are visualised.

Figure 18:
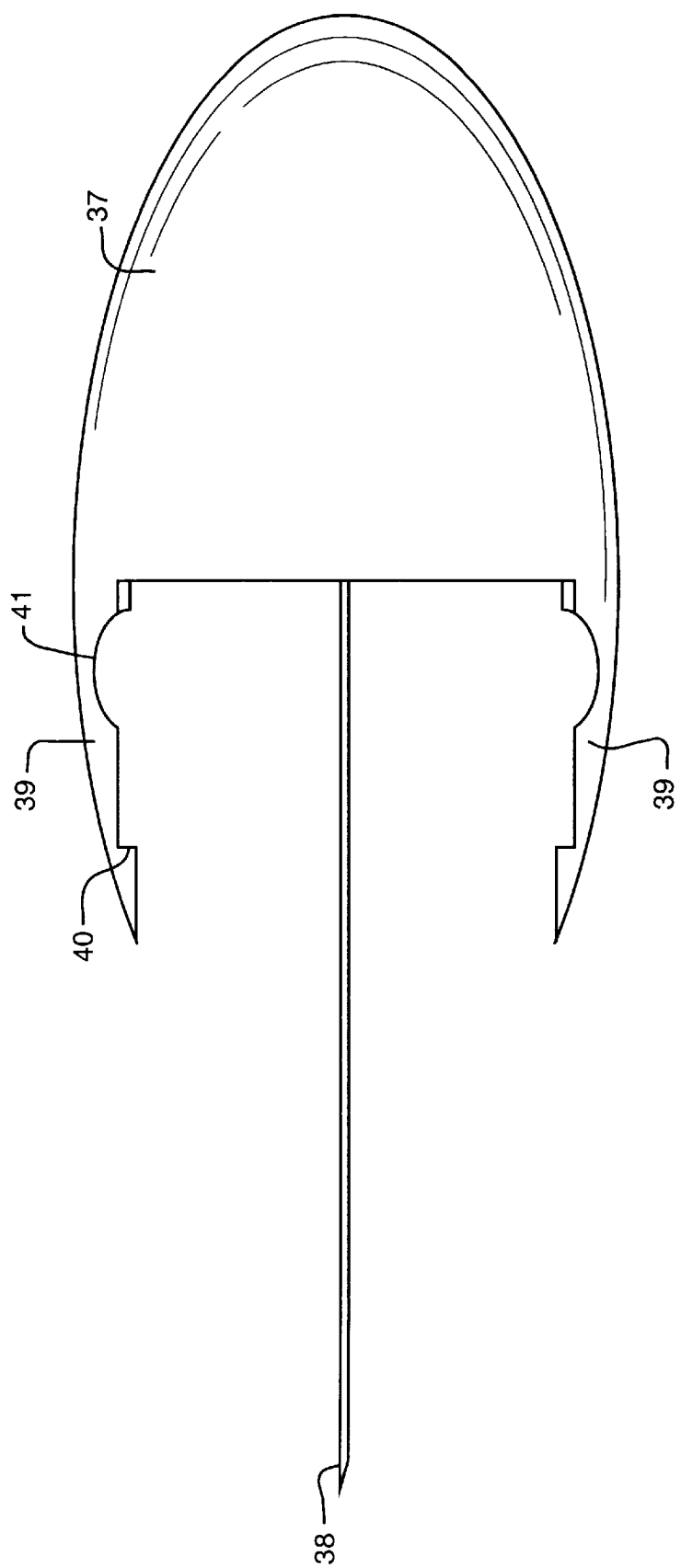
FIG. 18 is a top view of an insertion needle for use in connection with the device shown in FIG. 10.

From FIG. 18 an insertion needle 38 for use in connection with the device shown in FIG. 10 appears. The insertion needle comprises a needle hub 37 adapted to interact with housing in the same manner as the connector, i.e. by means of two elongate flexible elements 39. The needle extends through the soft cannula beyond the outer tip of this in the insertion position.

What is claimed is:

1. A subcutaneous infusion device comprising:

a housing;

a flow channel within the housing;

a cannula extending from the housing and being in flow communication with the flow channel;

a connector having a needle and adapted for delivery of fluid into the flow channel;

a guide element for guiding the connector with the needle into a correct position in relation to the housing;

said housing and said connector having respective guide surfaces arranged on a portion thereof and forming said guide means;

said guide surface on said housing defining a recessed portion of said housing extending along said flow channel;

said guide surface on said connector extending along said needle;

said guide surfaces including means for interlocking said connector and said housing upon insertion of said connector portion in said recessed portion;

said connector portion includes an elongate flexible element having a barb;

said recessed portion having a locking edge for interacting with said barb on the elongate flexible element; and wherein the elongated flexible element is placed so as to cover the needle in order to prevent injury thereby.

2. A subcutaneous infusion device as claimed in claim 1, wherein the elongated flexible element includes a bending area adapted to bring the barb out of engagement upon effecting a pressure on the flexible element thereby pivoting the flexible element.

* * * * *

UNITED STATES PATENT AND TRADEMARK OFFICE
CERTIFICATE OF CORRECTION

PATENT NO.   : 6,123,690
DATED        : September 26, 2000
INVENTOR(S)  : Jesper Mejslov It is certified that error appears in the above-identified patent and that said Letters Patent is hereby corrected as shown below:

<u>Claim 2,</u>
Line 2, delete "elongated" and substitute -- elongate -- in its place.

Signed and Sealed this

Thirtieth Day of October, 2001

Attest:

NICHOLAS P. GODICI
Attesting Officer    Acting Director of the United States Patent and Trademark Office